United States Patent [19]
Dietrich et al.

[11] Patent Number: 5,997,903
[45] Date of Patent: Dec. 7, 1999

[54] ORAL-ADMINISTRATION FORMS OF A MEDICAMENT CONTAINING PANTOPRAZOL

[75] Inventors: Rango Dietrich; Hartmut Ney, both of Constance, Germany

[73] Assignee: Byk Gulden Lomberg Chemische Fabrik GmbH, Konstanz, Germany

[21] Appl. No.: 08/167,961

[22] PCT Filed: Jun. 13, 1992

[86] PCT No.: PCT/EP92/01341

§ 371 Date: Dec. 17, 1993

§ 102(e) Date: Dec. 17, 1993

[87] PCT Pub. No.: WO92/22284

PCT Pub. Date: Dec. 23, 1992

[30] Foreign Application Priority Data

Jun. 17, 1991 [CH] Switzerland ................ 788/91

[51] Int. Cl.⁶ ..................................................... A61K 9/30
[52] U.S. Cl. .......................... 424/482; 424/464; 424/468; 424/471; 424/474; 424/484; 424/490
[58] Field of Search ..................... 424/482, 464, 424/468, 471, 474, 484, 490

[56] References Cited

FOREIGN PATENT DOCUMENTS

| | | |
|---|---|---|
| 0244380 | 11/1987 | European Pat. Off. . |
| 0247983 | 12/1987 | European Pat. Off. . |
| 0342522 | 11/1989 | European Pat. Off. . |
| 2189698 | 11/1987 | United Kingdom . |
| 2189699 | 11/1987 | United Kingdom . |

OTHER PUBLICATIONS

Remington's Pharmaceutical Sciences, 17th Ed, 1985, Mack Pub. Co., p. 1633–38.

*Primary Examiner*—Raj Bawa
*Attorney, Agent, or Firm*—Jacobson, Price, Holman & Stern, PLLC

[57] ABSTRACT

The invention relates to oral presentation forms for pantoprazole, which consist of a core, an intermediate layer and an outer layer which is resistant to gastric juice.

11 Claims, No Drawings

ORAL-ADMINISTRATION FORMS OF A MEDICAMENT CONTAINING PANTOPRAZOL

PRIOR ART

European Patent Application EP-A-244 380 describes oral presentation forms for acid-unstable active compounds from the class of $H^+/K^+$-ATPase inhibitors having a pyridylmethylsulphinyl-1B-benzimidazole structure, which have a core, an intermediate layer, and an outer layer which is resistant to gastric juice. European Patent Application EP-A-247 983 describes and claims the formulations disclosed in EP-A-244 380 in connection with the $H^+/K^+$-ATPase inhibitor omeprazole.

In the case of the presentation forms claimed in European Patent Applications EP-A-244 380 and EP-A-247 983, stabilization of the acid-unstable active compounds is achieved, in particular, by adding bases to the core and thus increasing the pH; to achieve an adequate storage stability, however, certain conditions must be maintained both during preparation and during storage, and these can be reconciled with an optimum pharmaceutical formulation and problem-free stock-holding only with difficulty. EP-A-247 983 thus appropriately states: "It is essential for long-term stability during storage that the water content of the presentation form containing the active compound omeprazole (tablets, capsules and pellets with a coating which is resistant to gastric juice) is kept low and is preferably not more that 1.5 wt. %. Final packs with pellets which have a coating which is resistant to gastric juice and are contained in hard gelatine capsules accordingly are preferably to be provided with drying agents which reduce the water content of the gelatine shells to the extent that the water content in the pellets does not exceed 1.5 wt. %".

The water content, which is to be kept low during preparation of pellet cores for stability reasons, thus means that the mass to be extruded for preparation of the pellet core is no longer sufficiently plastic for the extrudate subsequently to be rounded off into spherical particles. Rather, cylindrical bodies are formed, which, during the subsequent coating step, receive thinner lacquer coatings on the ends and therefore do not have the required resistance to gastric juice at these points, and moreover do not protect the core reliably from the coating which is resistant to gastric juice by a sub-coating, which is essential for the stability.

The stability problems described also arise if attempts are made to formulate the $H^+/K^+$-ATPase inhibitor pantoprazole (prop. INN for the compound 5-(difluoromethoxy)-2-[(3,4-dimethoxy-2-pyridyl)methylsulphinyl]-1H-benzimidazole) as described in European Patent Applications EP-A-244 380 and EP-A-247 983.

DESCRIPTION OF THE INVENTION

It has now been found, surprisingly, that if certain fillers and binders often used as tablet auxiliaries, such as are mentioned for the preparation of the pellet and tablet cores in European Patent Applications EP-A-244 380 and EP-A-247 983, are dispensed with, the stability problems described do not occur. These fillers and binders are, in particular, lactose, microcrystalline cellulose and hydroxypropylcellulose.

The invention thus relates to a medicament in pellet or tablet form which contains the active compound pantoprazole, is to be administered orally, is resistant to gastric juice and consists of a basic pellet core or tablet core, one or more inert, water-soluble intermediate layer(s) and an outer layer which is resistant to gastric juice, and which is characterized in that the core contains, in addition to pantoprazole or in addition to a pantoprazole salt, polyvinylpyrrolidone and/or hydroxypropylmethylcellulose as the binder, and if desired mannitol additionally as an inert filler.

For a basic reaction of the pellet core or tablet core—if the desired increase in pH has not already been achieved by using the active compound salt - an inorganic base is admixed to this. Examples which may be mentioned here are the pharmacologically tolerated alkali metal, alkaline earth metal or earth metal salts of weak acids and the pharmacologically tolerated hydroxides and oxides of alkaline earth and earth metals. Sodium carbonate may be mentioned as an example of a base which is to be singled out.

In addition to the filler and binder, other auxiliaries, in particular lubricants and release agents, as well as tablet-disintegrating agents, are also employed in the preparation of the tablet cores.

Examples of lubricants and release agents which may be mentioned are the calcium salts of higher fatty acids, such as e.g. calcium stearate.

Possible tablet-disintegrating agents are, in particular, chemically inert agents. (Transversely) crosslinked polyvinylpyrrolidone (e.g. Crospovidone) may be mentioned as a preferred tablet-disintegrating agent.

In respect of the water-soluble intermediate layer(s) to be applied to the pellet core or tablet core, reference may be made to those water-soluble layers such as are usually used before application of layers which are resistant to gastric juice, or such as are described e.g. in DE-OS 39 01 151. Examples which may be mentioned of film polymers which can be used for the intermediate layer are hydroxypropylmethylcellulose and/or polyvinylpyrrolidone, to which plasticizers (such as, for example, propylene glycol) and/or other additives and auxiliaries (e.g. buffers, bases or pigments) can also be added if desired.

The expert knows, on the basis of his technical knowledge, what outer layers which are resistant to gastric juice can be used. Aqueous dispersions of suitable polymers which are resistant to gastric juice, such as, for example, a methacrylic acid/methyl methacrylate copolymer, if desired with the addition of a plasticizer (e.g. triethyl acetate), are advantageously used (to avoid organic solvents and since the core according to the invention does not have the sensitivity to water known from the prior art).

The active compound pantoprazole is known from European Patent 166 287. Examples of salts of pantoprazole which may be mentioned are the salts mentioned in European Patent 166 287. The sodium salt is a preferred salt.

The use of mannitol as the sole filler for tablets requires a suitable binder, which must impart an adequate hardness to the core. The polyvinylpyrrolidone used as a binder for preparation of the core is, in particular, a product of higher molecular weight (about 300,000 to 400,000). PVP 90 (molecular weight about 360,000) may be mentioned as a preferred polyvinylpyrrolidone.

Compared with the presentation forms known from the prior art for other $H^+/K^+$-ATPase inhibitors having the pyridylmethylsulphinyl-1H-benzimidazole structure, the oral presentation form according to the invention is distinguished, in particular, in that a water content in the tablet core in excess of 1.5 wt. % does not lead to discoloration (decomposition) of the active compound. Stable tablets are thus obtained even with a relatively high residual moisture content (of e.g. 5 to 8 wt. %) in the granules.

Pellets can be obtained by application of a preliminary isolation to sucrose starter pellets and subsequent application of a 30% solution of the active compound in isopropanol with hydroxymethylpropylcellulose as the binder.

The isolation layer can also be applied, analogously to tablets, using corresponding ready-made dispersions (e.g. opadry). The coating with a layer which is resistant to gastric juice is carried out by a procedure analogous to that for tablets.

The following formulation examples illustrate the invention in more detail, without limiting it.

EXAMPLES

1. Tablets

I. Tablet core

| | | |
|---|---|---|
| a) | Pantoprazole-Na sesquihydrate | 45.1 mg |
| b) | Sodium carbonate | 10.0 mg |
| c) | Mannitol | 42.7 mg |
| d) | Crospovidone | 50.0 mg |
| e) | PVP 90 (povidone) | 4.0 mg |
| f) | Calcium stearate | 3.2 mg |
| | | 155.0 mg | a) is mixed with some of b), c) and d). The remainders of b) and c) are added to a clear aqueous solution of e) and the pH is brought to >10 with b). Granules are obtained with this solution in a fluidized bed. The remainder of d), and f) are added to the dry granules and the granules are pressed on a suitable tablet-making machine.

II. Preliminary isolation (intermediate layer)

| | | |
|---|---|---|
| g) | HPMC 2910, 3 cps | 15.83 mg |
| h) | PVP 25 | 0.32 mg |
| i) | Titanium dioxide | 0.28 mg |
| j) | LB Iron oxide yellow 100 E 172 | 0.025 mg |
| k) | Propylene glycol | 3.54 mg |
| | | 20.00 mg |
| | Total weight per preisolated core | 175.00 mg | g) is dissolved in water and h) is added and also dissolved (A). i) and j) are suspended in water using a suitable stirrer (B). A and B are combined. After addition of k), the suspension is sieved immediately before further processing, during which the tablet cores obtained under I. are coated with an adequate layer thickness of the suspension in a suitable apparatus.

III. Coating with a layer which is resistant to gastric juice

| | | |
|---|---|---|
| l) | Eudragit ® L 30 D | 13.64 mg |
| m) | Triethyl citrate | 1.36 mg |
| | | 15.00 mg |
| | Total weight per film-coated tablet resistant to gastric juice | 190.00 mg | l) is diluted with water and m) is added. The dispersion is sieved before processing.

III. is sprayed, in suitable apparatuses, onto the preisolated cores obtained under II.

2. Pellets

I. Starter pellets

| | | |
|---|---|---|
| a) | Sucrose pellets (0.7–0.85 mm) | 950.0 g |
| b) | Hydroxypropylmethylcellulose | 50.0 g | a) is sprayed with an aqueous solution of b) in a fluidized bed (Wurster process).

II. Active pellets

| | | |
|---|---|---|
| c) | Pantoprazole-Na sesquihydrate | 403.0 g |
| d) | Hydroxypropylmethylcellulose | 40.3 g | c) and d) are dissolved in succession in 30% isopropanol, and the solution is sprayed, in a fluidized bed (Wurster process), onto 900 g of the starter pellets obtained under I.

III. Preliminary isolation (intermediate layer)

The coating operation is carried out by a procedure analogous to that described for the tablets, in a coating pan or in a fluidized bed.

IV. Coating with a layer which is resistant to gastric juice

The coating operation is carried out by a procedure analogous to that described for the tablets, in a coating pan or in a fluidized bed.

Capsules of suitable size (e.g. 1) are then filled with the pellets.

We claim:

1. An orally administerable medicament in pellet or tablet form which is resistant to gastric juice, and in which each pellet or tablet consists of a core in which active compound or its physiologically-tolerated salt is in admixture with binder, filler and, optionally, a member selected from the group consisting of another tablet auxiliary and a basic physiologically-tolerated inorganic compound, an inert water-soluble intermediate layer surrounding the core and an outer layer which is resistant to gastric juice, wherein the active compound is pantoprazole, the binder is polyvinylpyrrolidone and/or hydroxypropylmethylcellulose and, optionally, the filler is mannitol.

2. Medicament according to claim 1 in tablet form, wherein polyvinylpyrrolidone and/or hydroxypropylmethylcellulose is the binder and mannitol is the filler.

3. Medicament according to claim 1 in pellet form, wherein polyvinylpyrrolidone and/or hydroxypropylmethylcellulose is the binder.

4. Medicament according to claim 1, wherein pantoprazole-sodium is the physiologically tolerated active compound salt.

5. Medicament according to claim 1, wherein pharmacologically tolerated alkali metal, alkaline earth metal or earth metal salt of a weak acid or pharmacologically tolerated hydroxide or oxide of an alkaline earth or earth metal is the basic, physiologically tolerated inorganic compound.

6. Medicaments according to claim 1, wherein sodium carbonate is the basic, physiologically tolerated inorganic compound.

7. A core of an orally-administrable medicament in pellet or tablet form wherein pantoprazole or a physiologically-tolerated salt thereof, as an essential active component, is in admixture with binder, filler and, optionally, a member selected from the group consisting of another tablet auxiliary and a basic physiologically-tolerated inorganic compound;

the binder being polyvinylpyrrolidone and/or hydroxypropylmethylcellulose.

8. A core of claim 7 wherein the filler is mannitol.

9. A core of claim 7 wherein the core is the core of a tablet.

10. A core of claim 9 wherein the essential active component is pantoprazole-sodium.

11. An orally administrable medicament in pellet or tablet form and which is resistant to gastric juice, wherein each pellet or tablet consists of:

a) a core in which an active compound or a physiologically tolerated salt thereof is in admixture with binder, filler and, optionally, a member selected from the group consisting of another tablet auxiliary and a basic physiologically tolerated inorganic compound, b) an inert, water soluble intermediate layer surrounding the core, and c) an outer layer which is resistant to gastric juice;

the active compound being pantoprazole;

the binder being polyvinylpyrrolidone and/or hydroxypropylmethylcellulose; and the core being substantially free from lactose, microcrystalline cellulose and hydroxypropylcellulose.

* * * * *